United States Patent [19]

Schack et al.

[11] 4,216,338

[45] Aug. 5, 1980

[54] SYNTHESIS OF FLUOROCARBON ESTERS

[75] Inventors: Carl J. Schack, Chatsworth; Karl O. Christe, Calabasas, both of Calif.

[73] Assignee: The United States of America as represented by the Secretary of the Air Force, Washington, D.C.

[21] Appl. No.: 47,558

[22] Filed: Jun. 8, 1979

[51] Int. Cl.$^2$ .......................... C09F 7/00; C11C 3/00
[52] U.S. Cl. .................................... 560/227; 260/408
[58] Field of Search ......................... 560/227; 260/408

[56] References Cited

U.S. PATENT DOCUMENTS

| | | | |
|---|---|---|---|
| 2,792,406 | 5/1957 | Acker | 260/408 |
| 3,248,419 | 4/1966 | Hauptschein | 260/487 |
| 3,255,228 | 6/1966 | Hauptschein | 260/456 |
| 3,268,571 | 8/1966 | Mitsch | 260/456 |
| 3,291,843 | 12/1966 | Fritz | 260/408 |

*Primary Examiner*—John F. Niebling
*Attorney, Agent, or Firm*—Joseph E. Rusz; William J. O'Brien

[57] ABSTRACT

A method for synthesizing perfluoroesters by effecting a reaction at subambient temperatures between a perfluorocarbon acid, or its derivatives, and a halogen fluorosulfate to produce an intermediate perfluoroacyl hypohalite which in turn is reacted with a suitable olefinic reactant to produce a perfluoroester.

3 Claims, 1 Drawing Figure

SYNTHESIS OF FLUOROCARBON ESTERS

STATEMENT OF GOVERNMENT INTEREST

The invention and products described herein may be manufactured and used by or for the Government for governmental purposes without the payment of any royalty thereon.

BACKGROUND OF THE INVENTION

This invention relates to a process for synthesizing fluorocarbon esters. More particularly, this invention concerns itself with the development of a novel method for effecting the synthesis of perhalo or perfluoroesters which find use in a wide variety of military and space applications.

The synthesis of many simple fluorocarbon esters is extremely difficult because of the non-existence of suitable precursors. As a result, perhalo or perfluoroesters are relatively rare and their utilization as useful intermediates for a variety of chemical reactions has not been maximized even though their propensity for reacting easily and quickly in chemical synthesis procedures is well known. The most common chemical reaction for synthesizing esters utilizes the combination of an acid and an alcohol. Unfortunately, this simple and well known procedure cannot be utilized due to the fact that primary and secondary perfluoroalcohols are not stable. They decompose spontaneously through the elimination of hydrogen fluoride as demonstrated by the following reaction:

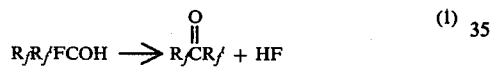
(1)

in which $R_f$ represents a perfluoroalkyl groups. All fluoroalcohols with a fluorine on the same carbon as the hydroxyl group are unstable due to HF elimination. Additionally, fluorinated esters of the type $R_fCO_2CFR_f'R_f''$ which contain fluorine on the alkoxy α—carbon are unstable in the presence of a fluoride ion at −78° or higher. Accordingly, these compounds cannot be formed by the reaction of perfluoroalkoxides with appropriate species such as acyl fluorides. The need for a simple and efficient process for producing fluorocarbon esters in order to take maximum advantage of their utilization as reaction intermediates, therefore, become obvious. Consequently, a considerable research effort has been undertaken in an attempt to provide a convenient route to the synthesis of simple perhalo esters. As a result of this effort, a novel, route for synthesizing these potentially very useful perhaloesters has been found. The route utilizes perfluoroacyl hypohalites as a novel reactant and involves reacting a fluorocarbon acid or its derivatives with a halogen fluorosulfate at subambient temperatures of about −20° or lower to produce an intermediate acyl hypohalite. This intermediate material is a reactive, positively polarized halogen species which will add to olefins readily in high yield to produce fluorocarbon esters. The resulting esters are thermally stable liquids useful as fluorocarbon solvents and fluids. They also find application as precursors to the preparation of the respective fluorocarbon ethers which are known to be fluids characterized by excellent high and low temperature properties.

SUMMARY OF THE INVENTION

In accordance with this invention, a novel route for the synthesis of perhaloesters has been discovered. The synthesis utilizes a perfluoroacyl hypohalite as a novel reactant which is characterized by its ability to effect an addition reaction with olefins to produce useful fluorocarbon esters. The synthesis involves a two step reaction conducted at subambient temperatures ranging from about −78° to −20° C. In the first step, a fluorocarbon acid, or one of its derivatives, is reacted with a halogen fluorosulfate as illustrated by the following equation:

(2)

wherein $R_f$ is a perfluoroalkyl group, M is an alkali metal or hydrogen and X is chlorine, bromine or iodine. The intermediate acyl hypohalite,

is then isolated. The intermediate is then reacted with a suitable olefin to produce the appropriate fluorocarbon ester. Equation (3), illustrates the typical reaction which takes place during the second step of the synthesis of this invention. The reactive, positively polarized, acyl hypochlorite intermediate reacts by addition across the C=C bond in the following manner:

(3)

This reaction serves as a convenient route for the synthesis of perfluoroesters.

Accordingly, the primary object of this invention is to provide a simple and expedient route for the synthesis of perhalo or perfluoroesters.

Another object of this invention is to provide a process for synthesizing perfluoroesters which utilizes acyl hypohalites as intermediate precursors in the synthesis of perfluoroesters.

The above and still other objects and advantages of the present invention will become more readily apparent after consideration of the following detailed disclosure thereof.

DESCRIPTION OF THE PREFERRED EMBODIMENTS

With the above-described objects in mind, the present invention involves a novel process for synthesizing perhalo and perfluoroesters. The compounds have been found to be especially useful as fluorocarbon solvents and fluids as well as for use as precursors for their respective fluorocarbon ethers which are known fluorocarbon fluids and polymers with excellent high and low temperature properties. Unfortunately, these materials are not utilized to their fullest reaction potential since they are relatively rare.

The most common ester yielding reaction is the reaction of an acid and an alcohol. This cannot be used for the synthesis of perhaloesters, however, due to the fact that primary and secondary perfluoroalcohols are unstable, decomposing spontaneously through the elimination of HF in accordance with the following reaction:

$$R_fR_f'FCOH \longrightarrow R_fCR_f' + HF \quad (4)$$
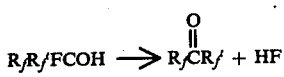

In addition, fluorinated esters of the type $R_fCO_2CFR_f'R_f''$ which contain fluorine on the alkoxy-α-carbon are unstable in the presence of fluoride ion at −78° C. or higher. Thus, they cannot be formed by the reaction of perfluoroalkoxides with appropriate species, such as acyl fluoride. All fluoroalcohols with F on the same carbon as the —OH group are unstable due to HF elimination.

With this invention, however, a new synthetic route to the preparation of very useful perhaloesters has been discovered which utilizes the perfluoracyl hypohalites as a novel reactant.

The synthesis is illustrated by the following general equation:

$$R_fCO_2M + XSO_3F \longrightarrow R_fCOX + MSO_3F \quad (5)$$
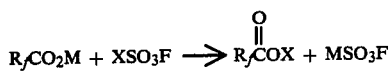

wherein $R_f$ is a saturated, straight or branched chain perfluoroalkyl group containing from one to ten carbon atoms, M is selected from the alkali metals or hydrogen and X is chlorine, bromine or iodine.

The reaction is conducted at subambient temperatures of from about −78° to −20° C. resulting in the production of an acyl hypochlorite as an intermediate. This intermediate is a reactive, positively polarized, halogen species which combines with olefinic compounds by way of an addition reaction to produce the corresponding perhaloester.

Equation (6) illustrates the reaction of the positively polarized chlorine species by its addition across C═C bonds in the following manner.

$$R_fCOCl + CF_2{=}CFCF_3 \xrightarrow{-78°} R_fCOCF_2CFClCF_3 \quad (6)$$
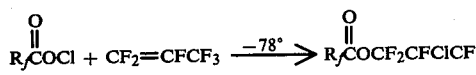

wherein $R_f$ is $CF_3$ or $ClCF_2$.

Equations 7A and B further illustrate the invention in which $R_f$ is $CF_3$ and M is Na=

$$CF_3CO_2Na + ClSO_3F \xrightarrow{-45°\,C.} CF_3CO_2Cl + NaSO_3F \quad (7A)$$
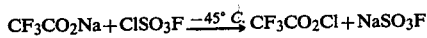

$$CF_3CO_2Cl + CF_3CF{=}CF_2 \xrightarrow{-78°\,C.} CF_3CO_2CF_2CFClCF_3 \quad (7B)$$
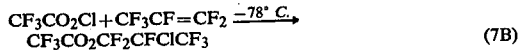

The reactions of equations 7A and 7B are further illustrated in Examples 1 and 2 which follow. Example 1 discloses the synthesis of the acyl hypochlorite $CF_3CO_2Cl$, while Example 2 discloses the use of the $CF_3CO_2Cl$ product of example 1 in preparing the perfluoroester $CF_3CO_2CF_2CFClCF_3$.

EXAMPLE 1

A 30 ml stainless steel cylinder containing $CF_3CO_2Na$ (5.24 mmol) was cooled to −196° and loaded with $ClSO_3F$ (2.93 mmol). The reaction cylinder was then maintained at −45° for 16 hr. The volatile products were separated by fractional condensation through a series of U traps cooled to −78°, −112°, and −196°. All material passed the −78° C. trap while the −196° trap contained 0.6 mmol of a mixture of $CF_3Cl$, $CO_2$, $COF_2$ and $Cl_2$. The material retained at −112° was a very pale yellow liquid. Removal of part of this material to another trap followed by careful warming resulted in decomposition to an equimolar mixture of $CF_3Cl$ and $CO_2$. The observed weight change (38 mg) of the solids in the cylinder agreed well with that calculated (41 mg) for the conversion of 2.93 mmol $CF_3CO_2Na$ to $NaSO_3F$. On one occasion, a sample of $CF_3CO_2Cl$, when allowed to warm to a temperature resulting in 40 mm vapor pressure, exploded in the vacuum line forming mainly $CF_3Cl$ and $CO_2$ but also some $COF_2$, $CF_4$, $C_2F_6$, and $Cl_2$. In carefully passivated IR cells which were pretreated with some $CF_3CO_2Cl$, a reproducible infrared spectrum of this acyl hypochlorite was obtained, $cm^{-1}$; 1844(S), 1308(M), 1241(S), 1206(S), 1093(S), 844(W), 765(W) and 719(MW): Decomposition rates varied considerably from minutes to hours depending on the sample. The primary decomposition product in the cells was $CF_3CO_2H$ indicating incomplete passivation of the cell.

EXAMPLE 2

To a 2.03 mmol sample of $CF_3CO_2Cl$ contained in a U-trap at −78°, hexafluoropropylene (2.72 mmol) was slowly added. After several hours the mixture was warmed to ambient temperature for 1 hour prior to fractional condensation through traps cooled to −78° and −196°. The −196° fraction consisted of one mmol $C_3F_3$ and 0.27 mmol each of $CF_3Cl$ and $CO_2$. The material retained at −78° was a colorless liquid and was identified as $CF_3CO_2CF_2CFClCF_3$ (1.70 mmol, 84% yield) on the basis of its vapor density molecular weight (297 found vs. 298.5 g/mol calculated), and controlled hydrolysis to a 1:1 mixture of $CF_3CFClCFO$ and $CF_3CO_2H$. Its spectroscopic properties confirmed this identification: infrared, $cm^{-1}$; 1856(S), 1335(M), 1297(S), 1249(VS), 1205(S), 1137(S), 1088(VS), 970(S), 850(W), 740(W), 671(MW): mass spectrum, 40 ev; m/e (assign., rel. intens.) 298(M, 0.01), 279(M—F, 0.03), 263(M—Cl, 0.03),
244(M—F, Cl, 0.05), 229(M—$CF_3$, 0.14), 185($C_3F_6Cl$, 4.7),
166 ($C_3F_6O$, 0.04), 163($C_3F_5O_2$, 0.06),
135($C_2F_5O$, $C_2F_4Cl$, 6.8), 131($C_3F_5$, 1.0),
119($C_2F_5$, 0.3), 116($C_2F_3Cl$, 1.8),
113($C_2F_3O_2$, 0.6), 109($C_3F_3O$, 0.1),
100($C_2F_4$, 3.3), 97($C_2F_3O$, 30),
94($C_2F_2O_2$, 0.7), 85($CF_2Cl$, 17), 81($C_2F_3$, 0.5),
78($C_2F_2O$, 0.9), 69($CF_3$, 100), 66($COF_2$, 1.7),
51(CFCl, 0.6), 50($CF_2$, 3.6), 47(COF, 3.5),
44($CO_2$, 3.6):

The reactions illustrated in equations 8A and 8B, as follows, further illustrate the invention when the $R_f$ moeity is $ClCF_2$ and M is H.

$$ClCF_2CO_2H + ClSO_3F \xrightarrow{-45°\,C.} ClCF_2CO_2Cl + HSO_3F \quad (8A)$$
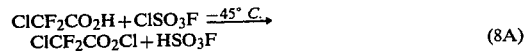

$$ClCF_2CO_2Cl + CF_3CF{=}CF_2 \xrightarrow{-78°\,C.} ClCF_2CO_2CF_2CFClCF_3 \quad (8B)$$
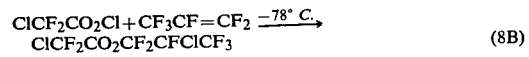

Examples 3 and 4 disclose the reactions 8A and 8B in greater detail. Example 3 illustrates the preparation of the acyl hypochlorite $ClCF_2CO_2Cl$. Example 4, on the other hand, illustrates the preparation of the perfluoroester $ClCF_2CO_2CF_2CFClCF_3$.

EXAMPLE 3

Chlorodifluoroacetic acid (2.80 mmol) was placed in a 30 ml stainless steel cylinder. After cooling to −196° and evacuating, ClSO₃F (2.91 mmol) was condensed in and the reaction allowed to proceed at −45° for two days. Separation of the products was effected by keeping the cylinder at −30° (to retain HSO₃F) and pumping the volatile materials through U traps cooled to −78° and −196°. The latter contained 0.24 mmol of Cl₂ and SO₂F₂, while the former contained the pale yellow liquid ClCF₂CO₂Cl. A sample of ClCF₂CO₂Cl allowed to stand at ambient temperature in the vacuum line for two hours, was found to have completely decomposed to an equimolar mixture of CF₂Cl₂ and Co₂. On one occasion a sample of ClCF₂CO₂Cl warmed to about 0° exploded when a valve was opened rapidly to allow it to expand. This contained explosion produced primarily CF₂Cl₂ and CO₂, but also some COF₂ and Cl₂.

EXAMPLE 4

Using the above described conditions of Example 3, ClCF₂CO₂Cl (2.30 mmol) was reacted with C₃F₆ (2.46 mmol) to furnish 0.60 mmol each of CF₂Cl₂ and CO₂ together with 0.76 mmol of unreacted C₃F₆. The colorless liquid ClCF₂CO₂CF₂CFClCF₃ (1.70 mmol, 74% yield) was identified spectroscopically: infrared cm⁻¹; 1856(S), 1300(MS), 1270(MS), 1238(VS), 1193(S), 1135(S),
1096(VS), 985,975(S, doublet), 848(W), 736(W), 690(W, br),
617(W): mass spectrum, 40 ev; m/e assign., rel. intens.) 314(M, 0.05), 295(M—F, 0.03), 279(M—Cl, 0.02), 245(M—CF₃, 0.02), 229(M—CF₂Cl, 0.15),
185(C₃F₆Cl, 31), 166(C₃F₆O, 0.41),
150(C₃F₆, 3.1), 147(C₃F₅O, 0.5),
135(C₂F₄Cl, 12), 131(C₃F₅, 2.4),
116(C₂F₃Cl, 3.8), 113(C₂F₃O₂, 2.9),
100(C₂F₄, 7), 97(C₂F₃O, 22), 94(C₂F₂O, 3.5),
85(CF₂Cl, 100), 78(C₂F₂O, 6), 69(CF₃, 55),
66(CFCl, 6), 50(CF₂, 12), 47(COF, 10), 44(CO₂, 24):

From a consideration of the above, it can be seen that the present invention provides a simple and efficient route for synthesizing perfluoroesters.

While this invention has been described with reference to preferred embodiments, it should be understood that various alterations and modifications as come within the purview of the appended claims are intended to be included herein.

What is claimed is:

1. A process for synthesizing perfluoroesters which comprises the step of first reacting:

(A.) a perfluorocarbon having the general formula $$R_fCO_2M$$

wherein $R_f$ is a saturated, straight, or branched chain perfluoroalkyl radical having one to ten carbon atoms and M is a member selected from the group consisting of an alkali metal and hydrogen; and (B.) a halogen fluorosulfate having the general formula $$XSO_3F$$

wherein X is a member selected from the group consisting of chlorine, bromine and iodine; and (C.) maintaining said reaction at a temperature of from about −78° C. to −20° C. for a period of time sufficient to produce an intermediate acyl hypohalite reaction products having the general formula $$\overset{O}{\underset{\|}{R_fCOX}}$$

(D.) effecting a second reaction between said hypohalite and an appropriate olefinic reactant at a temperature of from about −78° C. to −20° C. for a period of time sufficient to effect a reaction therebetween; and (E.) separating the resulting perfluoroester reaction product.

2. A process in accordance with claim 1 wherein said $R_f$ moiety is CF₃, said M moiety is sodium, said X moiety is chlorine, said olefinic reactant is CF₂=CFCF₃ and said first reaction is carried out at a temperature of −45° C. and said second reaction is carried out at a temperature of −78° C.

3. A process in accordance with claim 1 wherein said $R_f$ moiety is ClCF₂, said M moiety is hydrogen, said X moiety is chlorine, said olefinic reactant is CF₃CF=CF₂, and said first reaction is carried out at a temperature of −45° C. and said second reaction is carried out at a temperature of −78° C.

* * * * *